United States Patent [19]

Draenert

[11] Patent Number: 5,658,352
[45] Date of Patent: Aug. 19, 1997

[54] HIP PROSTHESIS AND ITS USE

[76] Inventor: Klaus Draenert, Gabriel-Max-Str. 3, D-8000, Munich 90, Germany

[21] Appl. No.: 595,510

[22] Filed: Feb. 1, 1996

Related U.S. Application Data

[63] Continuation of Ser. No. 466,326, filed as PCT/EP89/01054, Sep. 11, 1989, published as WO90/02533, Mar. 22, 1990, abandoned.

[30] Foreign Application Priority Data

Sep. 9, 1988 [DE] Germany ............... 38 307 48.0

[51] Int. Cl.$^6$ ................. A61F 2/32; A61F 2/30
[52] U.S. Cl. ...................... 623/23; 623/18
[58] Field of Search ............... 623/16, 18, 19, 623/20, 22, 23

[56] References Cited

U.S. PATENT DOCUMENTS

| | | | |
|---|---|---|---|
| 3,893,196 | 7/1975 | Hochman | 623/18 |
| 4,287,617 | 9/1981 | Tornier | 623/23 |
| 4,435,854 | 3/1984 | Keller | 623/23 |
| 4,536,898 | 8/1985 | Palfray | 623/33 |
| 4,589,883 | 5/1986 | Kenna | 623/22 |
| 4,608,053 | 8/1986 | Keller | 623/23 |
| 4,676,797 | 6/1987 | Anapliotis et al. | 623/18 |
| 4,808,186 | 2/1989 | Smith | 623/23 |
| 4,822,370 | 4/1989 | Schelhas | 623/23 |

FOREIGN PATENT DOCUMENTS

| | | | |
|---|---|---|---|
| 0 201 407 | 11/1986 | European Pat. Off. | 623/23 |
| 0 257 222 | 3/1988 | European Pat. Off. | 623/23 |
| 0257359 | 3/1988 | European Pat. Off. | 623/23 |
| 87 059 21.5 | 5/1988 | Germany | 623/23 |
| WO90/02533 | 3/1990 | WIPO | 623/23 |

*Primary Examiner*—David Isabella
*Attorney, Agent, or Firm*—Kinney & Lange, P.A.

[57] ABSTRACT

The invention relates to a hip joint prosthesis and its use in hip joint surgery. Essentially, the construction of the prosthesis is a laterally open hollow body whose cross-section (31) is horseshoe-shaped. This allows ideal adaption to the lines of load transfer. It is preferable for the prosthesis to comprise a laterally open hollow body as the stem (3), a more solid neck portion (2) and a head (1), which can be multidimensionally adjusted on the neck portion. The prosthesis can also be a complete implant with the construction of a straight-stemmed prosthesis having S-shaped mass distribution. (FIG. 1).

17 Claims, 8 Drawing Sheets

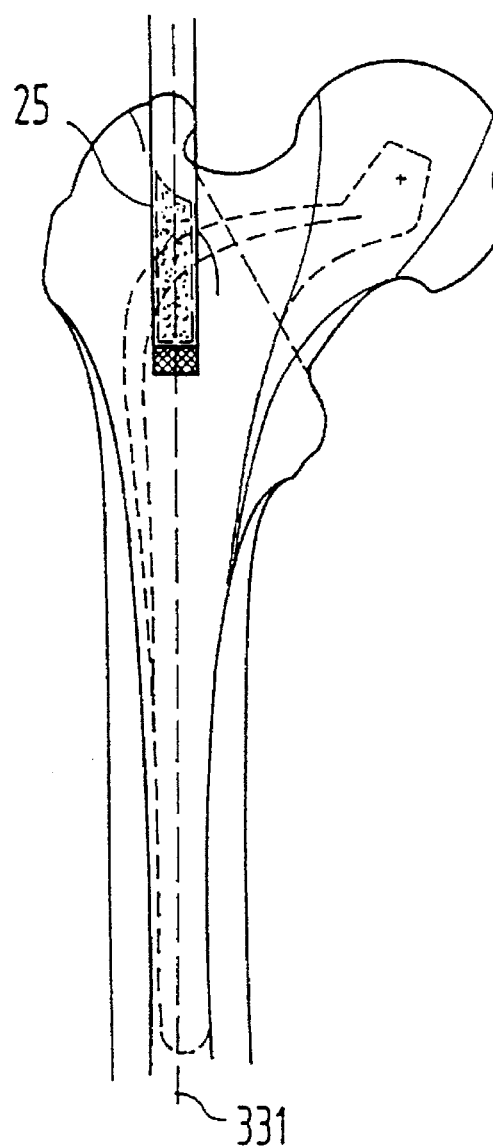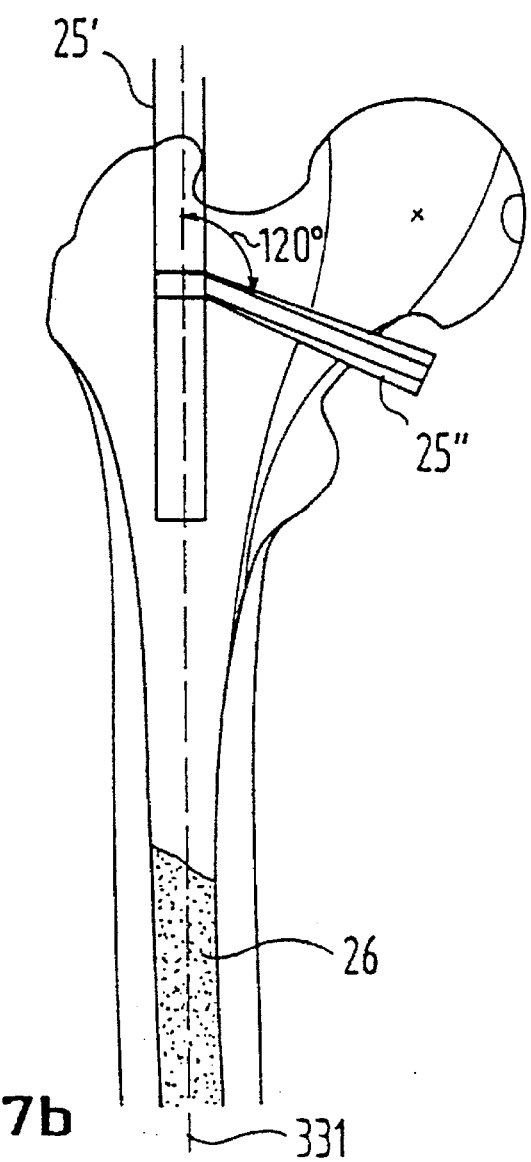
Fig. 7a
Fig. 7b

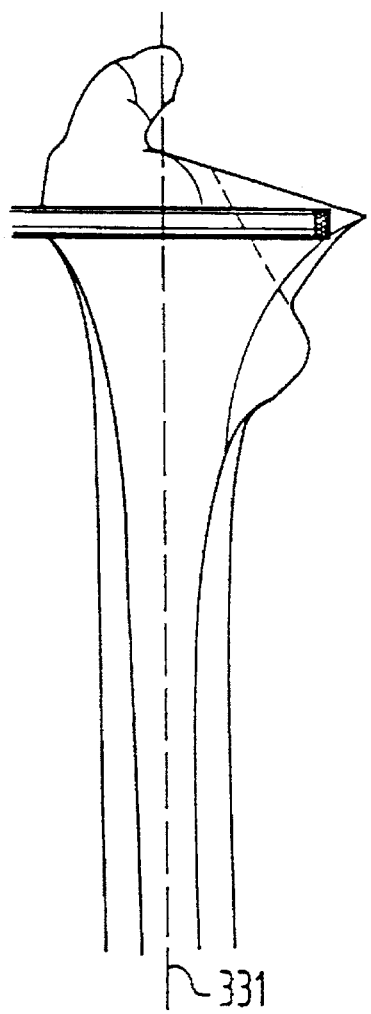
Fig. 7c
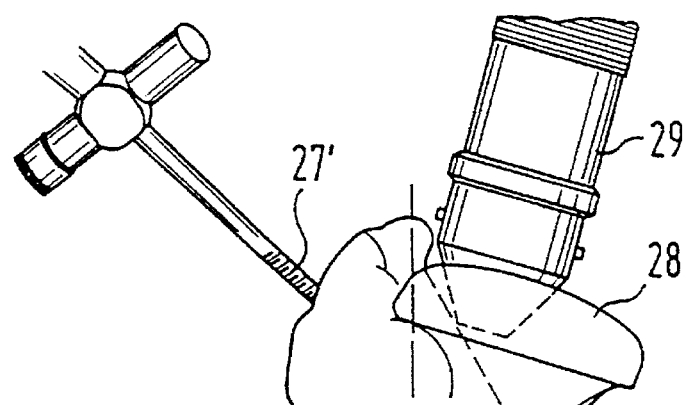
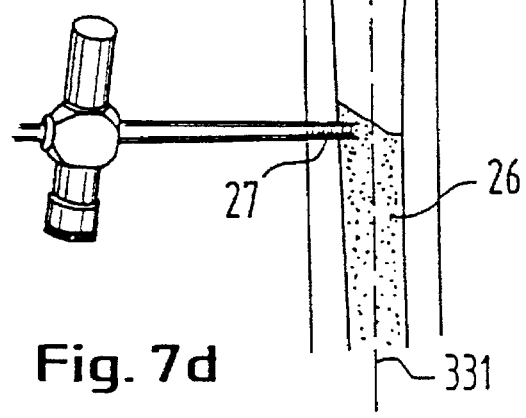
Fig. 7d

HIP PROSTHESIS AND ITS USE

This is a continuation of application Ser. No. 07/466,326, filed as PCT/EP89/01054, Sep. 11, 1989, published as WO90/02533, Mar. 22, 1990, now abandoned.

BACKGROUND OF THE INVENTION

This invention relates to a hip prosthesis that is preferably implanted using bone cement, but can also be implanted without using cement.

Joint replacement surgery has become standard therapy in the field of orthopaedic surgery, yet the prostheses that have been used to date and the processes for anchoring them cannot be considered as giving the final solution to the problems that arise during surgery. For example, cemented joint replacement components very often destroy the cement socket, whereupon the prosthesis loosens. This has led to the construction of a number of prostheses that can be implanted without the use of cement. However, the known prostheses of this kind still have their drawbacks. It was, for instance, discovered that cement-free implants can cause pain shortly after surgery, followed by uncontrolled atrophy around the bone, which may, in turn, cause pathological fractures (see I. W. Brown and P. A. Ring, Osteolytic changes in the upper femoral shaft following porous-coated hip replacement, J. Bone Joint Surg. 67B, pages 218 to 221). Furthermore, cement-free prostheses have by no means reduced the number of loose implants, but rather increased it.

In experiments on the hip joint, especially the femur, it has been possible to show that the cement-free components cause considerable deformation of the bone when it is under strain. The greater the mass of the implant, or the greater the deformability of the individual bone, the higher the degree of deformation. Yet in cement-free implants it is imperative to ensure positive contact with the bone from the very beginning. This fact has led to the development of positive or anatomically adapted components (see J. Henssge, Metbode zur Entwicklung anatomisch richtiger Implantatkörper, in "Grenzschichtprobleme der Verankerung von Implantaten unter besonderer Berücksichtigung von Endoprothesen", edited by M. Jäger, M. H. Hackenbroch, H. J. Refior, Georg Thieme Verlag Stuttgart, New York, 1981). One extreme aspect of this development is the so-called "custom-made prosthesis" as introduced by Mulier, for example (J. C. Mulier, Improvements of the Charnely technique of total hip replacement and future developments, Acta. Orthop. Belg. 52, pages 392 to 403). However, the design of this prosthesis made it particularly heavy. The bone reacted accordingly with especially severe deformation. However, bone deformation leads to surface movement and thus to bone resorption, which may cause the prosthesis to loosen.

Attempts have also been made to apply the findings on other implants to the field of prostheses. One of the results was that the principle of prestressing, which is one of the basic principles of osteosynthesis techniques, was introduced into the field of endoprostheses, as was the so-called press-fit principle (M. E. Müller, Total hip replacement: planning, technique and complications, in: Cruess, R. L. Mitchell, N. S.: Surgical management of degenerative arthritis of the lower limb, Chapter 10, pages 91 to 113, Lea & Febiger, Philadelphia 1975; M. E. Müller and B. Elmiger: Coxarthrose, 10-Jahres-Ergebnisse der sog. Setzholz-Totalprothese, Orthopäde 8, pages 73 to 74, 1979; K. Zweymüller, Knochen- und Gelenkersatz mit biokeramischen Endoprothesen, Facultas, Vienna 1978). Yet, just like the rigid prosthesis components, the principle of prestressing could not induce the bone to react in any other way but with severe deformation.

Long-term studies in more or less stably cemented prostheses have indicated the superiority of cemented components. The fact that the bony bed had been slightly remodelled was a sign of uniform load transfer, and the positive bone contact proved that there was no relative movement in the interface. This implies that the implant caused only slight deformation of the bone (K. Draenert, Histomorphologische Befunde zur gedämpften und ungedämpften Krafteinleitung in das knöcherne Lager, Vereinigung Nordwestdeutscher Orthopäden, 36th Annual Conference, Hannover, 15th to 18th Jun. 1986).

SUMMARY OF THE INVENTION

Thus the object underlying the invention is to provide a prosthesis (endoprosthesis) or an implant with which it is possible to achieve and reproduce good results as regards settling and load bearing capacity.

In order to achieve the object, the invention has been based on the principle that the construction of the prosthesis has to take into account the relationship between the degree of deformation and mass of implant and the deformability of the bone. The invention has been able to show that the dampened introduction of forces not only leads to reduced deformation of bone, but even considers that bone deformation varies, or can be varied, considerably from individual to individual. One way of achieving this is by designing the prosthesis in a special way or by reinforcing the bone with bone cement.

The above object is achieved by the prosthesis according to the invention. The prosthesis according to the invention takes into account and solves the problems of bone deformation via the implant.

A further subject matter of the invention is the use of the hip prosthesis according to the invention and a process for anchoring the same.

The prosthesis according to the invention is characterised by the fact that it makes use of the largest surface available for load transfer onto the prosthesis or the bone, and that it exhibits maximum rotation stability. The prosthesis and its mass can be adapted to the specific deformability of the bone and, in extreme cases, can have a lightweight construction.

The prosthesis according to the invention can be used in such a way that only little bone is lost. In the process for inserting the prosthesis, the first step is to grind a slot using a diamond grinding or cutting tool. The cement is applied via an anchoring channel, also using a diamond grinding tool, whilst applying high vacuum. In cement-free implantation, the construction of the prosthesis according to the invention allows it to be prestressed, and thus it can guarantee that porous or ceramic-coated implants will be held in a mechanically firm position for the time it takes the bone to grow in.

In an embodiment of the invention, the prosthesis of the invention comprises a laterally open hollow body that contacts the load-supporting structures and constitutes an open, hollow-bodied implant. In this case, the rigidity of the prosthesis preferably decreases from the proximal region to the distal region.

Hollow-bodied implants as such are basically known. EP-A-190 446, for instance, discloses a metal bone implant comprised of two tin shells or bowls joined together to give a hollow body. Being a hollow body, the weight of the implant is reduced, yet it is essentially as rigid as conventional implants and does not solve the aforementioned problems that occur in connection with load transfer and the deformability of the bone.

EP-A-65 481 discloses a hip prosthesis having a hollow stem. The stem has hole-shaped recesses and thus exhibits local material fatigue, which is used to adapt its longitudinal rigidity or bending strength to the longitudinal rigidity or bending strength of the surrounding bone. This implant is not in a position to solve the aforementioned problems either.

Another known prosthesis is a cementless, self-locking hip prosthesis out of whose full stem holes are cut, thus leaving only thin struts that connect the medial and lateral portions of the prosthesis (S. Tepic, S. M. Perren, Cementless self-locking stem for hip prosthesis).

In contrast, one embodiment of the prosthesis of the invention comprises along the side of the stem and, optionally, along the neck, a continuous opening or groove that is shaped as an elongated slot and runs along almost the entire length of implant, preferably along more than 80% or, if necessary, more than 90% of the implant length. In this region, the prosthesis has a U-shaped or horseshoe-shaped cross section, wherein the strut of the U or the horseshoe forms the medial portion of the prosthesis and the arms of the U have rounded tips. The open parts of the prosthesis are situated where there is no or only slight load transfer. Thus the prosthesis offers the largest possible surface for load transfer, but with a smaller mass, and it can be adapted in various ways to the individual needs of the patient. The depth of the groove can be up to 90% of what the prosthesis measures when extended in the medial/lateral direction, preferably about 30 to 80%, most preferably about 40 to 70%, and the depth can vary in the longitudinal direction. In the scope of the invention, the groove can also be very shallow and fine. In extreme cases, and provided the design of the prosthesis, especially the distribution of its mass, ensures that the object of the invention is achieved, the groove can be done away with altogether, turning the prosthesis into a complete implant.

The prosthesis of the invention preferably has a head portion, a neck portion and the stem.

The head is preferably a semicircular shell that covers only the supporting roof of the femoral head, because load transfer is restricted to this area. To accommodate joint movement during walking, it is preferable for the front (ventral) and back (dorsal) parts of the sliding plane to be drawn down a little lower.

The head portion can also be a complete replacement. It is either mounted onto a cone in the neck of the prosthesis, or it is provided with a cone itself and can be inserted in the neck. It is also possible for the head portion to be welded or mounted directly onto an elongated and preferably solid plateau of the neck portion.

The neck of the prosthesis is more solid and, optionally, a completely solid body. It constitutes the junction to the grooved stem, whose cross-section is preferably U-shaped, but can also be used to receive a joint portion, which is a slide rail, or an insert or detachable component, in cases where modular implant components are to be used. In this embodiment, it is also possible to replace the semicircular shell of the supporting plane with a conventional insert cone. Provided part of the neck of the femur is still there, it is also possible to slip an appropriately modified head over it, which maintains a considerably larger load-bearing surface at the neck of the femur. The prosthesis can, however, be a one-piece product; the neck portion is then supported by the rough structured cancellous bone compartment of the femoral neck.

In another embodiment of the invention, the head portion, or the cone that receives the head, is adjustable or slidable in three dimensions at the neck portion. For example, a head that is movably mounted on an insert rail can be adjusted in the frontal plane and/or sagittal plane. In this way it is possible to adjust exactly one alignment for different configurations of patients. The term alignment means the exact aligning of the head in the direction of load transfer to the sacro-iliac joint, which receives the load in a physiological manner and transfers it to the spine. The design of the aligning means is preferably such as to allow independent adjustability in each individual direction, thus ensuring greatest possible freedom and adaptability during alignment.

The head can be fastened in any desired position, for example by means of regulating screws. The neck portion can also be adjusted in length, by which exact adjustment can be achieved with respect to the load plane or centre of rotation. The load plane can be constructed considering the centre of the greater trochanter, the centre of rotation and the symphyseal centre.

The cross-section of the stem is preferably an open, semicircular tube, or along its circumference it is a ½ to ¾, preferably a ⅔ to ¾, closed tube, with a conical taper in the direction of the prosthesis tip. It is essential that the stem be exactly laterally inserted along the axis of the medullary canal without causing any unnecessary damage to the structures of the femoral neck. The semicircular tube or the hollow groove contacts the strong bone structure of the proximal cross-section of the femur with its portion that is convex in cross-section.

In one embodiment of the invention, the mass distribution in all the cross-sectional planes of at least the proximal section is such that the main mass is dorsally and medially aligned. This has been done because systematic studies using x-ray pictures have shown that major load transfer occurs in these areas. As a result of this asymmetry, it is usually necessary to produce a right-hand version and a left-hand version of the prosthesis.

The medial alignment of the mass gradually decreases towards the distal end of the prosthesis. In the distal half of the prosthesis, the medial and lateral mass distribution is essentially symmetrical as regards the axis. The dorsal alignment of the prosthesis mass decreases rapidly towards the distal end of the prosthesis. In the distal half of the prosthesis, the mass is in essentially ventral alignment. The side view shows that the dorsal-ventral mass distribution is essentially S-shaped: the dorsal mass excess in the proximal region drops to zero in the middle prosthesis section and drops to negative in the distal prosthesis section, i.e. there is a ventral mass excess, which turns to zero at the tip of the prosthesis. Nevertheless, the prosthesis is still a straight-stemmed prosthesis, because the entire prosthesis axis, for example its straight axis of construction from the drive-in point to the tip of the prosthesis, runs through the prosthesis. The above-mentioned mass distribution ensures that all the intersection planes of the prosthesis are optimally adapted to the shape of the shaft of the femur and that the prosthesis fits well.

The proximal section of the medial longitudinal edge of the prosthesis comprises a concave curve. The curve is more pronounced than in conventional prostheses, and its radius is preferably under 10 cm or under 8 cm, more preferably around 4 to 6 cm. This longitudinally concave portion of the prosthesis fits exactly to the load-bearing structure of the medial portion of the femur. The mass distribution, i.e. the thickness along the longitudinal section of the prosthesis, along this concave surface is preferably such that the main mass is proximally distributed, i.e. distributed adjacent to the head, and then preferably decreases continuously from that point onwards to the tip. This has been done because experiments have shown that load transfer is concentrated proximally, which means that the prosthesis mass must also be concentrated in this region. The whole gravity centre of the prosthesis mass is preferably within the bone, thus preventing unwanted rocking movements and moments of torsion.

The centre of gravity of the prosthesis is preferably placed in its proximal portion either dorsally or medially. It can also be situated inbetween. As a result of the decrease in mass, the stiffness of the prosthesis also decreases from the proximal region to the distal region.

Studies have shown that a high moment of retrotorsion occurs during the "heel strike" phase, when the heel touches the ground, i.e. the head is turned backwards, whereas there is only a slight moment of antetorsion during the toe-off phase. In order to achieve high rotational stability, these moments must be taken up by the "projections" or "arms" of the prosthesis' horseshoe-shaped cross-section. Particular attention should be paid to the projection of the hollow groove in the proximal region. Here the stem of the prosthesis can comprise wing-shaped projections that achieve extremely high rotational stability. In right/left prostheses, the shape of the wings can also be asymmetric. In this case, it is preferable for the dorsal wing or arm to be widened and, if necessary, lengthened. As explained above, this is because the major rotation component constitutes a retrotorsion of the prosthesis, which begins when the heel touches the ground and ends when the leg is no longer in motion. Also, by shortening the ventral wing it is possible to cut down on material without any loss in the strength of the fixation.

Biopsy results have shown that by varying the thickness of the stem, it is possible to determine the best and most solid version of the prosthesis in view of deformation. For this purpose, a bone sample, which could be cylindrical in shape, is removed and the individual deformability of the bone measured. This is followed by determining the density of the bone via calibrated X-rays. The bone's deformation behaviour can be determined from the individual deformation of the bone and its density. Low deformability allows the option of using a cement-free prosthesis. In cases of high deformability, it is preferable to use a cemented prosthesis.

At sites where stress concentration occurs, particularly proximally, the prosthesis must comprise a thicker wall than elsewhere, and the bone cement sheath, too, must be thicker to ensure even load transmission and to avoid unwanted deformation of the bone.

The tip of the prosthesis is such that it displays wide bearing surfaces in the lateral direction, especially in the ventral direction. There are no edges or burrs that could give rise to concentrated stress and thus induce stress-caused fractures of the cement sheath.

In a simple embodiment, the prosthesis comprises a cone-shaped receiving member for any kind of spherical head, such as a commercially available head made of steel or ceramic. The variability of the medial shape of the femoral component in this embodiment corresponds to the low variability of the medial structure in the individual femur. Thus it is enough to supply three to four different prosthesis sizes to cater for the common morphological variants of the hip joint. The number of sizes can be reduced even further if a variable receiving member adjustable in the frontal plane is provided at the neck of the femur. If necessary, said member can also be adjustable in the sagittal plane and/or in height.

The determination of the size of the prosthesis is preferably based on the distance between the axis of the femur shaft at the level of the minor trochanter and the supporting structure at the medial femur.

The basic axis or column of the construction constitutes the axis of the femur's shaft. The shaft or stem of the prosthesis is constructed in such a manner that it is led along this axis until it has a firm fit. This can be achieved either via the length of the stem or via the above-discussed profile of the cross-section.

The prosthesis can also be constructed such that several components are arranged on top of one another at a hollow or groove-shaped axis, thus providing a modular system.

The length of the prosthesis can be varied and is usually between 13 and 22 cm. The length is to be especially variable if the prosthesis constitutes a modular system.

The modular construction kit system, wherein the axis is a half-open tube or a hollow groove that receives the modular components, offers decisive advantages if surgery has to be repeated because each component can be individually replaced.

In cement-free implantation, the prosthesis can also be pre-stressed before being inserted. This is particularly preferable if one wishes to ensure that porous or spongiosa-like structured surfaces will be integrated in a bony manner, and if relative movements are to be avoided. For this purpose, the prosthesis is fixed on the head and then distally locked, or the process is carried out the other way around. Although this prestress is almost lost within the next three months, it guarantees stable fixation by means of bony in-growth during this period.

The prosthesis can be cast or forged of a conventional Co—Cr—Mo alloy. It can also be made of titanium or a Ti alloy. It is also possible to make the prosthesis completely porous in order to increase the surface in the way the spongiosa metals do, or the prosthesis can be prepared with a porous, ceramic, bioglass or apatite coating.

The stem of the prosthesis can preferably also be made of coated grids that are spot-welded or welded together via supporting ribs.

BRIEF DESCRIPTION OF THE DRAWINGS

The drawing shall serve to explain the invention in greater detail. The figures show.

If not otherwise specified, each drawing shows the front view of the (implanted) prosthesis.

DETAILED DESCRIPTION OF THE PREFERRED EMBODIMENTS

Figure 1:
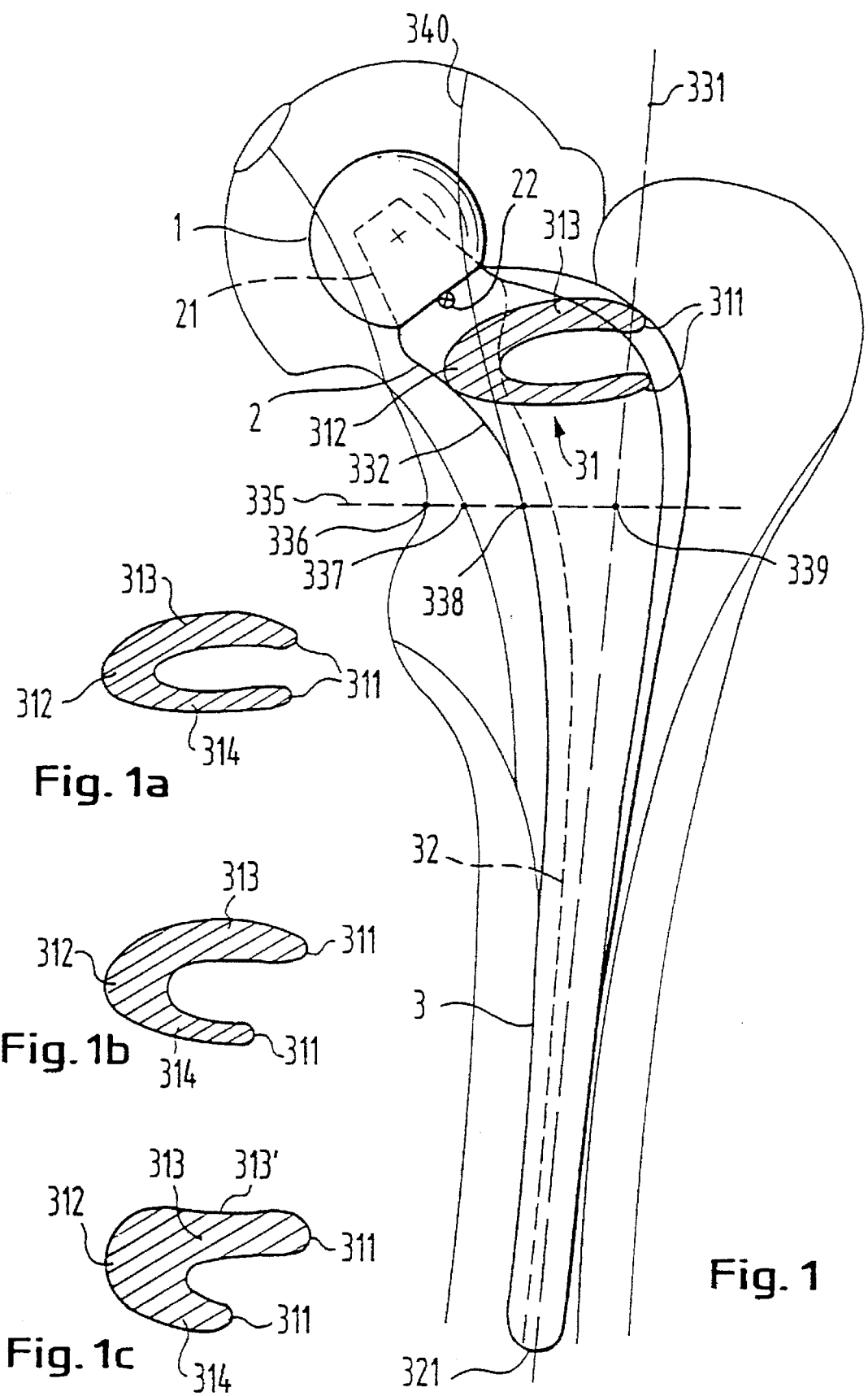
FIG. 1 an embodiment of the inventive prosthesis inserted in the femur, wherein the cross-section of the prosthesis has been diagrammatically drawn in for the purpose of clarity, FIGS. 1a to 1c typical cross-sections through the prosthesis, e.g. in the proximal region of the stem, FIG. 2 a further embodiment of the prosthesis according to the invention with a semicircular shell, wherein various cross-sectional planes have, too, been diagrammatically drawn in, FIG. 3 a further embodiment of the prosthesis according to the invention showing diagrammatical cross-sectional planes, FIGS. 4a to 4b various embodiments showing the displaceability of the insert cone, FIGS. 5a and 5b a front and side view of a further embodiment of the prosthesis according to the invention, FIG. 6 a prosthesis according to the invention constructed as a modular system and FIGS. 7a to 7d various stages during insertion of a prosthesis according to the invention.

The prosthesis according to FIG. 1 is diagrammatically illustrated in the femur and comprises an insert head 1 made of ceramic or steel that sits on the cone-shaped portion 21 of the neck 2 of the prosthesis, the angle to the shaft axis being 120° to 150°. This angle can be adjusted via an axis 22 and can be firmly positioned, or it is determined by the construction, this usually being 140°.

The neck 2 is firmly welded to the stem 3. In the medial longitudinal direction, the stem 3 comprises a concave curve 332 that adapts itself to the supporting structures in the medial femur, the structures being directed to the supporting roof. These structures can be made visible by X-ray, for instance. According to Wolff's Law, the bone adapts itself to the load it has to carry. Thus the direction of the load or load transfer can be determined from the direction of the supporting structures or trabecula. The shape of the concave curve 332 does justice to this fact.

In the longitudinal section, which is diagrammatically shown in FIG. 1, see the dotted line 32, the part of the prosthesis that is medial to line 32 being solid, the prosthesis comprises a solid neck and a layer or wall thickness that decreases in the distal direction. The tip 321 of the prosthesis is round.

With the help of an X-ray, the size of the prosthesis is determined on the basis of the shaft axis 331, which preferably runs through the drive-in point of the prosthesis, and the minor trochanter intersection plane 335 (shown as a dotted line). The minor trochanter intersection plane 335 results from the horizontal load plane in the knee joint and is usually inclined to the shaft axis at an angle of 81°. Point 339 is where the minor trochanter intersection plane 335 intersects the shaft axis 331. Point 338 is where the minor trochanter intersection plane 335 intersects the line 340 of load transfer or the projection line of the supporting structure. Point 337 is where the minor trochanter intersection plane 335 intersects the inner (endosteal) cortical bone or the edge of the medullary cavity. Point 336 is where the minor trochanter intersection plane 335 intersects the bone at the hollow of the transition to the minor trochanter, where the insertion attachment of the muscles is to be found. The size of the prosthesis to be used results either directly from the distance between points 339 and 338, or is indirectly determined from the distance between points 339 and 337 or 339 and 336.

The cross-section of the stem, which has been diagrammatically drawn in as number 31 for instance, is preferably ellipsoid, parabolic, U-shaped or horseshoe-shaped and, if necessary, can also comprise a (three-leafed) clover-shaped profile. The ends 311 of the arms of the U or of the horseshoe are blunt and rounded. The mass distribution or the wall thickness of the cross-section is preferably eccentric, with enlargements being provided both medially (at 312) and dorsally (at 313), because load transfer takes place mainly there.

In the typical cross-section of the proximal region of the prosthesis shown in FIG. 1a, the dorsal arm or wing 313 and the ventral arm or wing 314 of the prosthesis cross-section are essentially the same in length, whereas in the embodiment according to FIG. 1b, the ventral arm or wing 314 is shorter than the dorsal arm or wing 313. This makes it possible to save material without a substantial loss in stability, because load transfer mainly takes place in the medial and dorsal region.

In the embodiment of the cross-section according to FIG. 1c, the outside of the dorsal arm 313 comprises a concave wing with a recess 313'. This gives further improved rotational stability.

Figure 2:
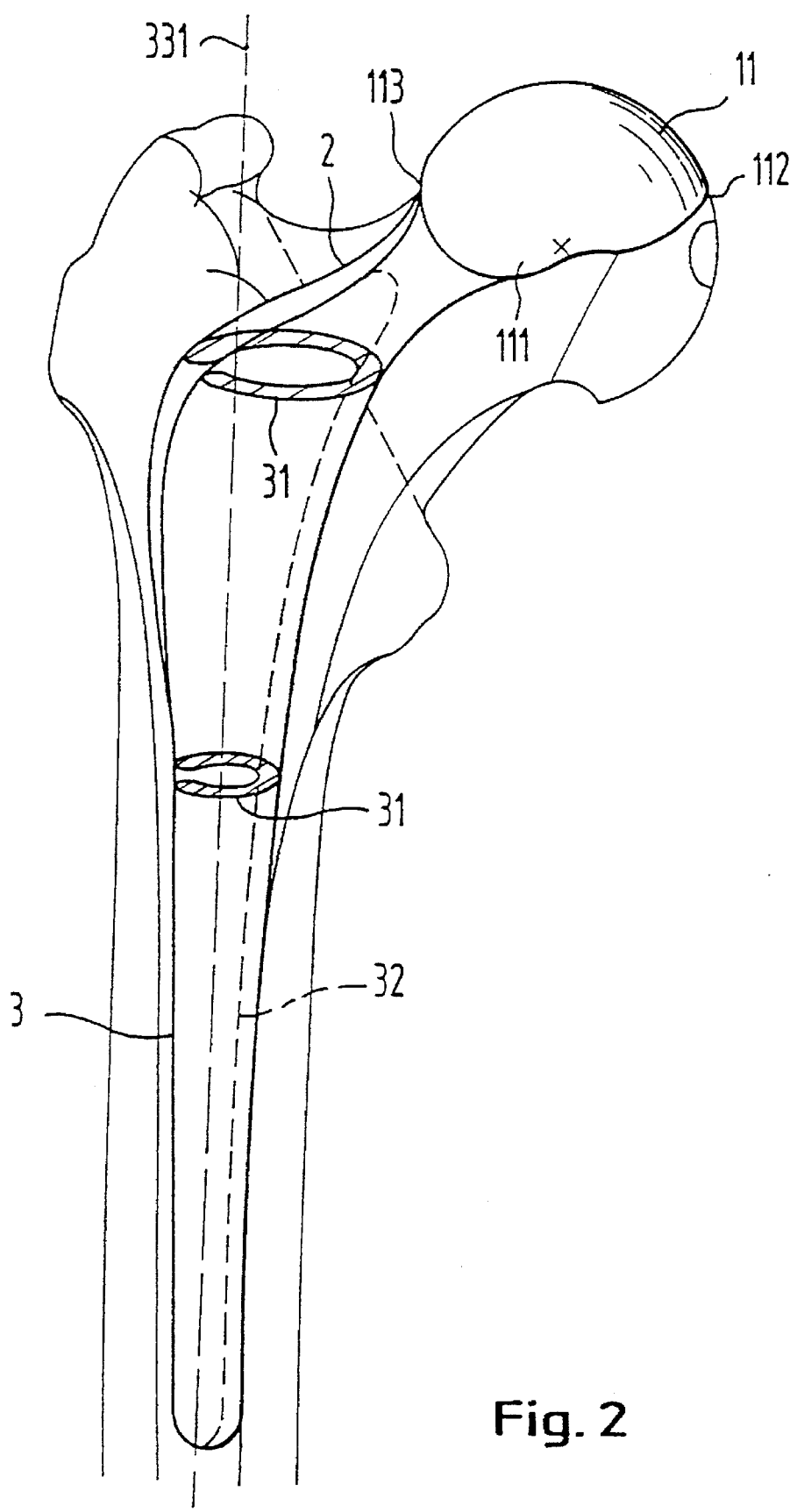

If not specified otherwise, the right-hand prosthesis shown in FIG. 2 is similar in structure to the left-hand prosthesis according to FIG. 1.

In the prosthesis shown in FIG. 2, there is a semicircular bowl or shell 11 mounted in a rigid or jointed fashion on the neck 2, which is firmly welded to the stem 3. This semicircular shell is spherical and comprises ventrally and dorsally distended surfaces 111.

The medial end 112 of the cap is preferably a retracted blunt edge level with the fovea capitis, to which a ligament is attached. The solid lateral end 113 of the shell merges into the firm, preferably solid neck. The shell becomes thinner towards the medial rim. If required, the shell can be a member mountable via a rail (not shown in FIG. 2) and is thus precisely adjustable. If required, the shell can also be inserted together with a cone into the neck 2 of the prosthesis in an adjustable manner.

The ceramic or steel head can, too, be firmly attached to a firm base of the neck 2.

Figure 3:
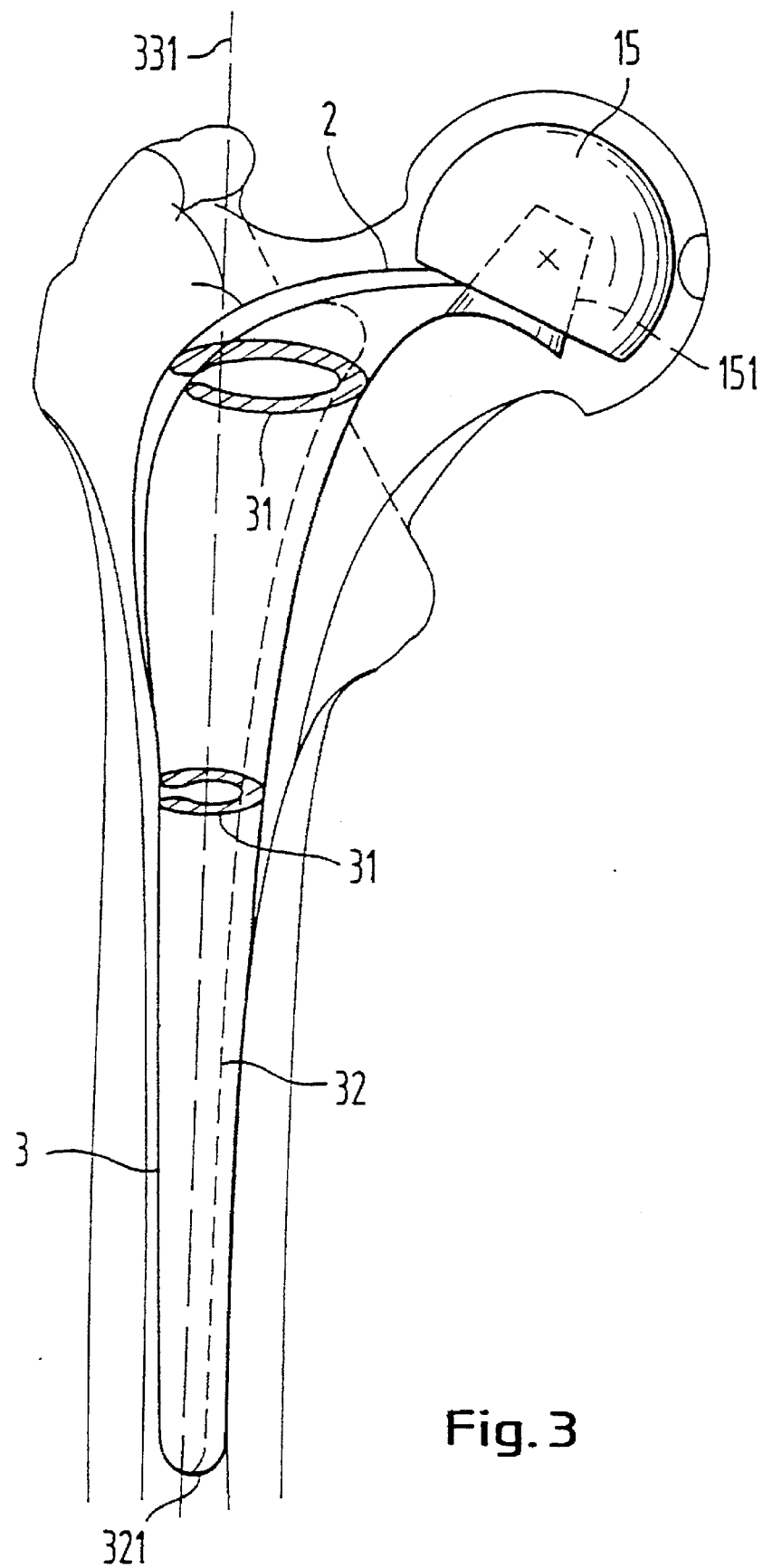

As in the prosthesis according to FIG. 3, the head 15 can also be mounted onto a cone 151 of the neck 2, which is solid in the proximal region.

Figure 4A:
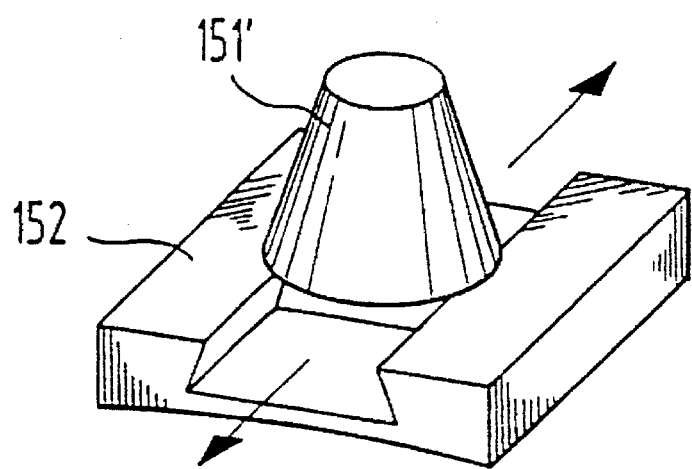
Figure 4B:
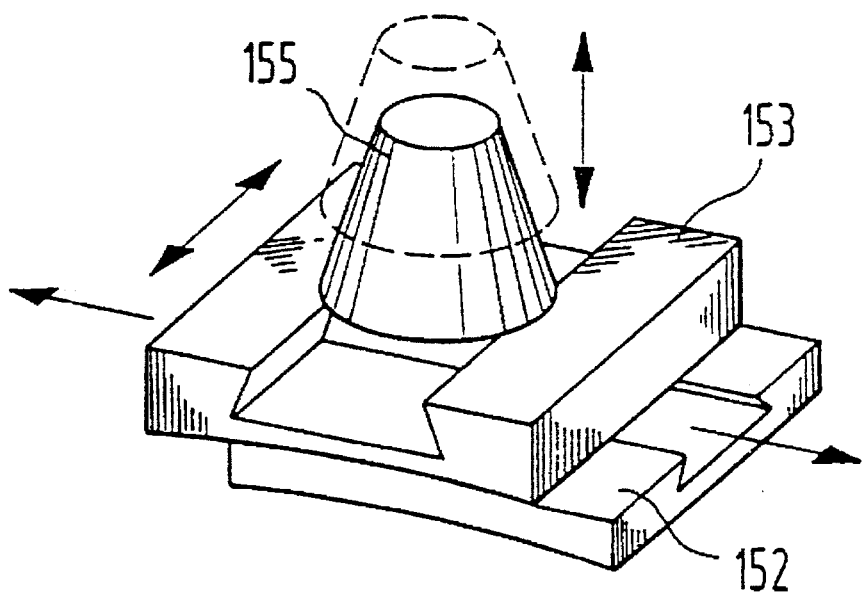

FIGS. 4a and 4b show that the shape of the neck can be such that the head is precisely adjustable in one, two or three planes.

According to FIG. 4a, there is an insert cone 151', onto which the head is mounted, on a rail 152 that is firmly welded to the solid neck of the prosthesis, which cone is movable in the frontal plane (parallel to the forehead) in the direction of the arrows. The rail may be a dovetail guide.

Instead of the embodiment according to FIG. 4a, the rail can also be curved, and the insert cone can also be tiltable in the sagittal plane (perpendicular to the forehead), preferably at an angle of 5° to 10° and dorsally, too.

According to FIG. 4b, the insert cone 155 for the head or shell is movable or tiltable in both the frontal plane and in the sagittal plane via two mutually perpendicular rails 152 and 153, and is also movable in the vertical direction (see the dotted area). Thus the cone, as shown by the arrows, can be adjusted in three planes and can be firmly fastened in any position by means of screws, for instance.

In addition to the embodiments shown only in diagram in FIGS. 4a and 4b, it is also possible to choose other means to render the head of the prosthesis adjustable in one, two or three directions or planes and to ensure perfect alignment.

Figure 5A:
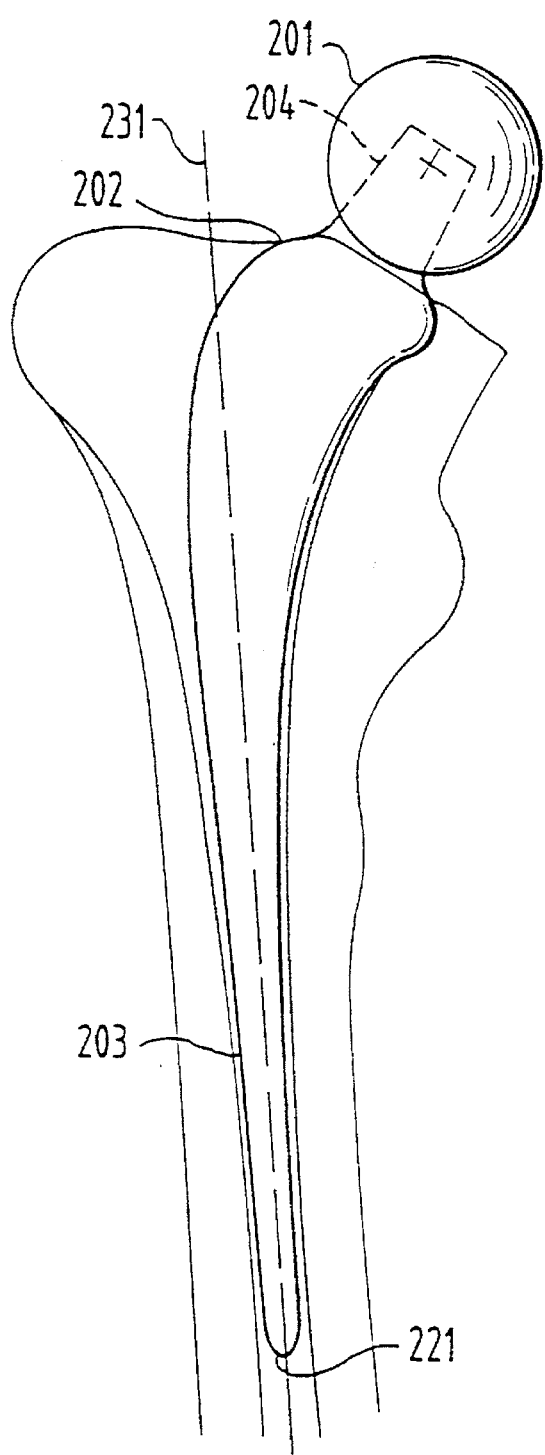
Figure 5B:
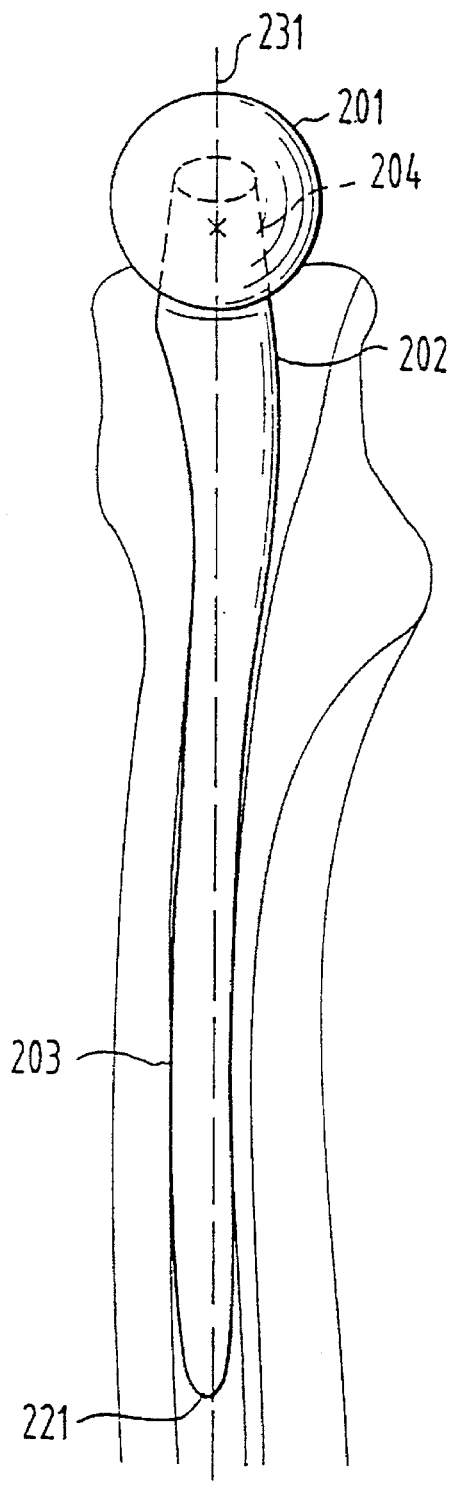

The embodiment of the prosthesis according to FIG. 5, which is shown in front view in FIG. 5a and in side view in FIG. 5b, is solid. The side view of the prosthesis comprises an S-shaped mass distribution, yet it is still a straight-stemmed prosthesis because the entire prosthesis axis runs through the body of the prosthesis.

The prosthesis according to FIG. 5 also comprises a head 201, a neck 202 and a shaft 203. The head 201 sits on a cone-shaped portion 204 of the neck 202. The prosthesis axis is represented by number 231. The front view according to FIG. 5a shows that in the proximal section of the prosthesis, the gravity centre of the mass is well within the medial region and, towards the distal end of the prosthesis, is slowly approaching the axis. In the distal third of the prosthesis, the medial and lateral mass distribution of the prosthesis is essentially symmetrical.

The side view according to FIG. 5b shows that the gravity centre of the mass is well within the dorsal region in the neck of the prosthesis 202 and in the proximal portion of the shaft of the prosthesis 203, but that the prosthesis exhibits an S-shaped curve towards the distal end. In the approximate middle of the prosthesis, the dorsal and ventral mass distribution is almost symmetrical, whereas the lower half of the prosthesis exhibits ventral mass distribution. Mass distribution is most ventral at the point which is approximately 1/5 to 1/6 of the length of the prosthesis away from the tip of the prosthesis 221, whereas it begins to move back in the direction of the axis 231 of the prosthesis towards the tip of the prosthesis 221. The prosthesis design according to FIG. 5 ensures an excellent fit in the medullary canal, and in spite of its S-shaped design, the prosthesis can still be driven into the bone in the same manner as a straight-stemmed prosthesis. This is because the S-shape is such that the entire prosthesis axis 231 runs through the body of the prosthesis.

Figure 6:
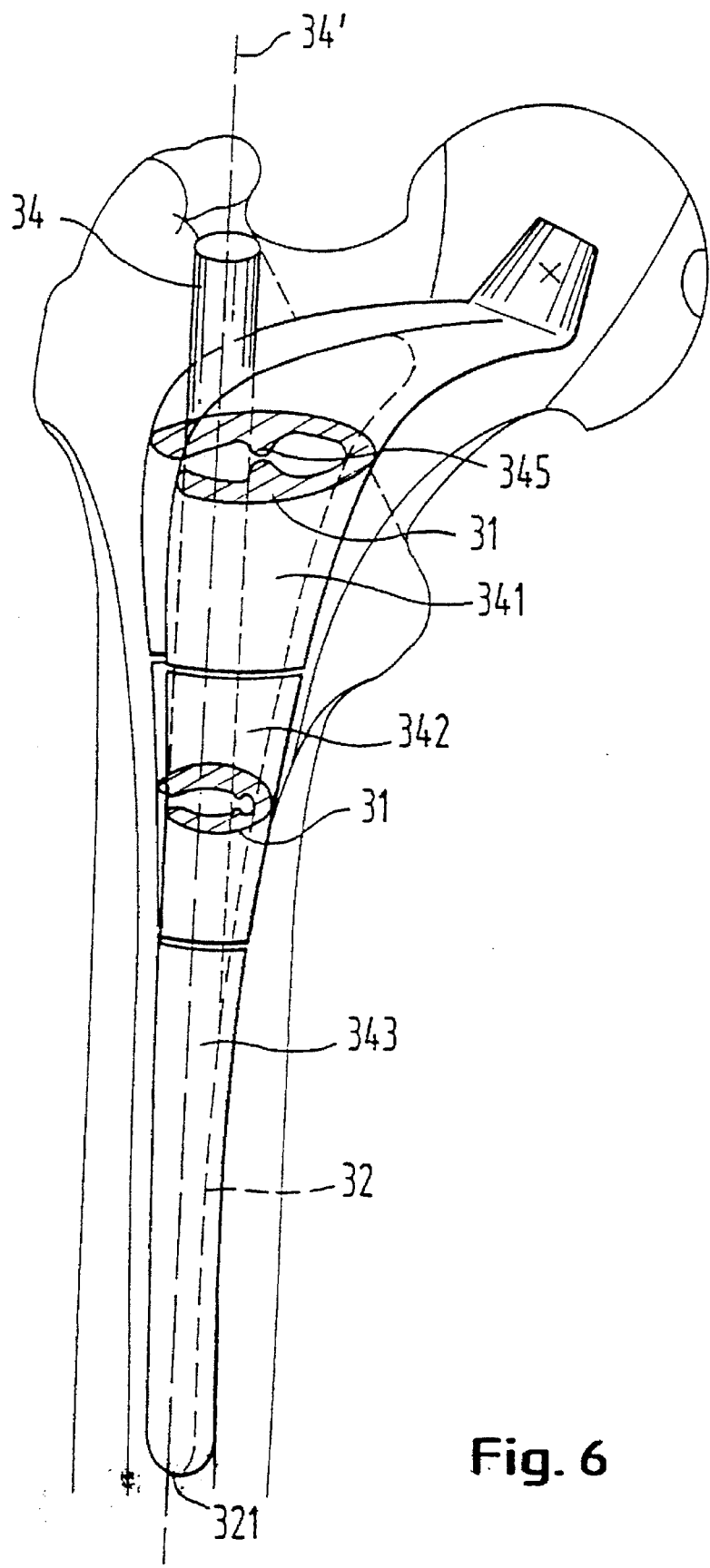

FIG. 6 is a diagram of a modular system type prosthesis. It is composed of a lateral axis 34 arranged in the medullary cavity axis 34' and medial insert components 341, 342 and 343. As component 341 shows, the components comprise a guide 345 that surrounds the axis 34, wherein the shape of the components has been adapted to the axis 34. The components are also shaped as hollow bodies having a horseshoe-shaped cross-section (see cross-sections 31).

EXAMPLE

FIGS. 7a to 7d show various phases of the insertion of the prosthesis according to the invention.

A patient suffering from advanced arthrotic changes in the hip joint is to receive an artificial joint. Two X-rays (anterior-posterior and axial) with a faded-in scale are taken of the hip joint, whereupon an endoprosthetic replacement is designed. After the appropriate prosthesis has been chosen and the conventional preparatory measures for surgery have been taken, the patient undergoes surgery, and the affected hip joint is exposed. After the joint capsule has been opened and partially removed, the ligament of the femoral head is cut and the femoral head luxated. After the rest of the capsule has been removed, the straight extension of the medullary cavity between the trochanter major (greater trochanter) and the neck of the femur is opened using a diamond cutting tool in a wet-grinding process, such as that according to EP-A-99 371; an approximately 14 mm annular defect having a depth of approximately 50 mm, the cortico-spongious bone cylinder can be removed using a special extractor, also such as that according to EP-A-99 371, whereupon a long hollow cylinder grinder is used to prepare the medullary cavity by wet-grinding it (see FIG. 7a showing the hollow cylinder grinder 25).

Once the bony bed has been cleaned using pressure lavage, a guide instrument 25' is inserted that uses a template 25'' to ascertain the exact cutting plane for removing the head of the femur (see FIG. 7b). Distally the medullary cavity is closed by a plug 26. Once the head has been resected, a concave diamond cutter of 10 mm in diameter is used to mill a cross cut in the frontal direction from the lateral direction to the medial direction in the horizontal plane of the Calcar femoris (medial intersecting edge of the neck of the femur) (see FIG. 7c). The defect is closed again using a press-fit inserted, but shorter bone cylinder.

The cylinder that was removed to open the medullary cavity is then washed and placed back into position, and then distally displaced using a plastic plunger. 2 cm below the planned tip of the prosthesis and after stab incision and insertion of a trocar, the medullary cavity is anterolaterally opened and a self-cutting cannula 27, such as that according to EP-A-305 417, is screwed into the compact substance of the bone. A Kirschner wire is pushed through the cannula. The bone cylinder is pushed forward from the proximal direction until the Kirschner wire wobbles. The wire is then pulled back out, the plug is pushed forward another 2 cm and the cannula is turned a further three turns. Once the bed of the bone has been prepared in this manner, it receives the sample prosthesis to check the fit of the permanent prosthesis. As soon as the prosthesis fits ideally and contacts a large surface of the medial spongiosa, it is removed. Then a drainage cannula 27' is also screwed into the dorsal half of the ridge of the greater trochanter, and both cannulae are connected to a vacuum pump that has not yet been switched on. The tube to the proximal cannula initially remains pinched off.

The medullary cavity is sealed off with a silicone seal, the bone cement syringe 29 is applied and the vacuum pump switched on (see FIG. 7d). By this the cement is evenly sucked into the bony bed, which is free of blood, and fills the spongiosa honeycombs in the supporting region. When the cement syringe is removed, the prosthesis is slowly pushed in until it reaches its determined position. When the self-curing bone cement has hardened, the acetabulum is inserted. The operation is terminated by repositioning the components of the femur and closing the wound layer for layer.

I claim:

1. A hip joint prosthesis comprising an elongated stem, a neck and a head, said prosthesis extending between a proximal end and a distal end and having a lateral side, a medial side, a ventral side and a dorsal side, said stem being configured to be implanted in a medullary cavity of a femur, said stem being hollow over at least a substantial fraction of the length of the stem, said hollow stem having a horseshoe-shaped cross-section with a medial wall portion, a dorsal wall portion and a ventral wall portion, wherein the cross-section is open at said lateral side of said prosthesis.

2. The prosthesis according to claim 1, wherein said ventral portion of the cross-section of the prosthesis is shorter than said dorsal portion.

3. The prosthesis according to claim 1, wherein the medial wall portion, the dorsal wall portion and the ventral wall portion of the hollow stem each have a medium wall thickness, and wherein, at least in a proximal section of the prosthesis, the dorsal wall portion and the medial wall portion of the hollow body have an enlarged thickness with respect to their respective medium wall thickness.

4. The prosthesis according to claim 1, wherein the wall thickness of the hollow body decreases from a proximal section to a distal section of said stem portion.

5. The prosthesis according to claim 1, wherein the prosthesis has a mass largely concentrated in a proximal end of the prosthesis and wherein the shape of the prosthesis is such that a centre of gravity of the mass lies outside the prosthesis.

6. The prosthesis according to claim 1, wherein the the cross-section has a mass centre of gravity which lies within the medial portion.

7. The prosthesis according to claim 1, wherein the stiffness of the prosthesis decreases from a proximal portion to a distal portion.

8. The prosthesis according to claim 1, wherein the stem defines a longitudinal axis, and wherein, at least in a proximal portion, a cross-section taken parallel to the longitudinal axis, comprises a concave arch.

9. The prosthesis according to claim 1, wherein said prosthesis is of modular construction and comprises an axial support and a plurality of components adapted for attachment to the axial support.

10. The prosthesis according to claim 9, wherein said prosthesis comprises a guide attached relative to the stem, the guide allowing the head to be detachably mounted relative to the stem.

11. A hip joint prosthesis according to claim 1 further comprising means for adjusting positional location of said head of the prosthesis with respect to the stem in at least one dimension.

12. The prosthesis according to claim 11, wherein positional location of said head portion of the prosthesis is adjustable in a frontal plane.

13. The prosthesis according to claim 11, wherein positional location of said head portion of the prosthesis is adjustable in a sagittal plane.

14. The prosthesis according to claim 11, wherein positional location of said head portion of the prosthesis is adjustable in a frontal plane and a sagittal plane.

15. The prosthesis according to claim 11, wherein positional location of said head portion of the prosthesis is adjustable in a vertical plane.

16. The prosthesis according to claim 11, wherein positional location of said head portion of the prosthesis is adjustable in a frontal plane, a sagittal plane and a vertical plane.

17. The prosthesis according to claim 11, wherein positional location of said head portion of the prosthesis is adjustable in a frontal plane and in a sagittal plane and in a vertical plane and in any combination thereof independently from each other.

* * * * *